United States Patent [19]

Bonne et al.

[11] Patent Number: 4,587,105
[45] Date of Patent: May 6, 1986

[54] INTEGRATABLE OXYGEN SENSOR

[75] Inventors: Ulrich Bonne, Hopkins; Robert G. Johnson, Minnetonka, both of Minn.

[73] Assignee: Honeywell Inc., Minneapolis, Minn.

[21] Appl. No.: 611,306

[22] Filed: May 17, 1984

[51] Int. Cl.[4] ............... G01N 27/12; G01N 27/46
[52] U.S. Cl. .................................. 422/98; 165/136; 204/425; 204/426
[58] Field of Search ............... 204/421–429; 422/98; 165/136

[56] References Cited

U.S. PATENT DOCUMENTS

| | | | |
|---|---|---|---|
| 3,396,079 | 8/1968 | Finzi et al. | 165/136 |
| 3,901,067 | 8/1975 | Boardman et al. | 422/98 |
| 4,020,830 | 5/1977 | Johnson et al. | 204/426 |
| 4,198,851 | 4/1980 | Janata | 422/98 |
| 4,220,685 | 9/1980 | Markow et al. | 165/136 |
| 4,224,280 | 9/1980 | Takahama et al. | 422/98 |
| 4,281,642 | 8/1981 | Steinberg | 165/136 |
| 4,338,281 | 6/1982 | Treitinger et al. | 422/98 |
| 4,351,182 | 9/1982 | Schmidberger | 422/98 |
| 4,401,967 | 8/1983 | Miwa et al. | 422/98 |

Primary Examiner—T. Tung
Attorney, Agent, or Firm—Omund R. Dahle

[57] ABSTRACT

An $O_2$ sensor built on a silicon chip which has a $SiO_2$ dielectric layer bridging over a depression in the surface of the chip. A $ZrO_2$ layer overlies the bridge and a pair of spaced apart palladium electrodes are on the surface of the $ZrO_2$. A heater for the $ZrO_2$ is embedded in the $SiO_2$ bridge.

16 Claims, 2 Drawing Figures

INTEGRATABLE OXYGEN SENSOR

BACKGROUND AND SUMMARY OF THE INVENTION

The present invention relates to the field of zirconium oxide oxygen sensors and particularly to a low cost, integratable absolute $O_2$ sensor apparatus. The present design is directed to minimize the heater power required to heat the $ZrO_2$ to operating temperature, to be adaptable for use with low voltage IC's, and to utilize only small amounts of noble metal electrodes while giving fast response time at low cost.

One type of electrode-active oxygen monitor is shown in the de Bruin et al U.S. Pat. No. 4,326,318 which discloses an electrolytic cell including an electrode of platinum and palladium, and an electrolyte of yttrium stabilized zirconia.

A gas detector for another gas such as CO or chlorine is shown in the Kimura U.S. Pat. No. 4,343,768, titled "Gas Detector," in which a recess is formed in a substrate below an upper film of electrically insulating substance.

Another oxygen sensor is taught in the Takao et al U.S. Pat. No. 4,107,019 titled "Solid Electrolyte Thin Film Oxygen Sensor Having Thin Film Heater." In this patent a ceramic substrate having a heater embedded in the substrate has on the surface of the substrate a sandwich construction of an electrically conductive film (partially oxidized metal), a layer of zirconium oxide electrolyte, and a surface metal usually of the platinum group metals.

In an embodiment of the present invention a silicon substrate has a $SiO_2$ layer formed thereon, the substrate having a depression in a main planar surface which depression is bridged over by the $SiO_2$ layer so that a hollow exists beneath a bridge portion of the $SiO_2$. The $SiO_2$ layer has embedded therein in the region of the bridging area a thin film conductive heater. Formed over the surface of the $SiO_2$ layer, particularly over the bridge area, is a solid electrolyte layer of zirconium oxide ($ZrO_2$) which has on the surface a pair of spaced electrodes of a noble metal such as palladium. The electrodes and the heater each have contacts adapted to be connected to an energizing and measuring circuit.

DESCRIPTION

Figure 1:
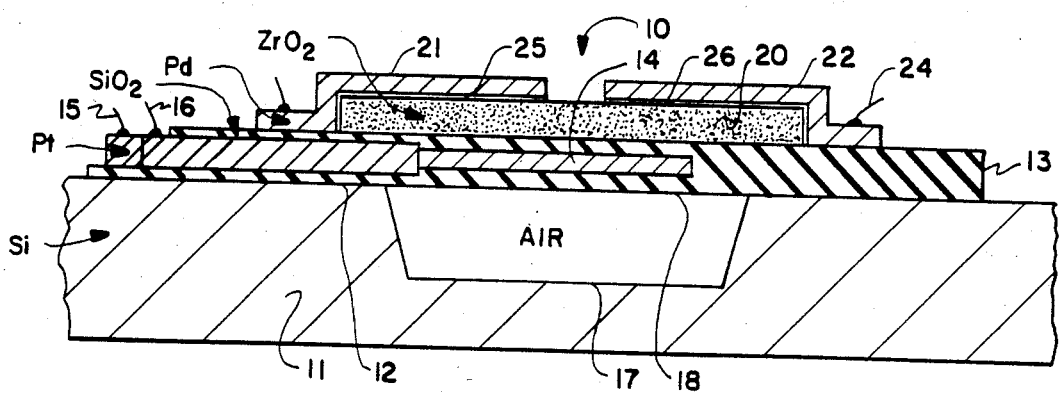
FIG. 1 is a cross sectional view of the $ZrO_2$ oxygen sensor structure according to the invention.

Referring now to FIG. 1, there is shown in cross section the general structural arrangement of an embodiment of the zirconium oxide oxygen sensor. In general, this is a micro sensor built on a bridge on a semiconductor chip. The semiconductor chip substrate may be silicon which has on its major surface a thin layer of dielectric, that is, a layer of silicon dioxide ($SiO_2$) or silicon nitride. A layer of zirconium oxide ($ZrO_2$) is formed over the $SiO_2$ layer and a pair of electrodes, spaced one from the other, are fabricated on the $ZrO_2$ surface. A depression is etched in the silicon substrate surface beneath the $SiO_2$ layer forming a bridge of $SiO_2$.

Specifically in FIG. 1 the sensor is shown at 10 and comprises a semiconductor substrate, such as silicon, 11 having a major planar surface 12 which has formed thereon a dielectric thin film layer 13. With a silicon substrate, the dielectric layer may be silicon dioxide or silicon nitride. Embedded or laminated within the dielectric layer is a sinuous electrically conductive heater member 14, preferably of platinum. The heater member 14 may be energized at terminals 15 and 16 from an external circuit. Etched beneath the dielectric layer in the substrate 11 is a depression 17 so that a void exists under the dielectric layer at the bridge area 18. The heater member 14 is also located at the bridge area. Over the top of the dielectric layer 13 at the bridge area is a solid electrolyte layer of stabilized zirconium oxide ($ZrO_2$) 20 which has ionic oxygen mobility. A pair of conductive films 21 and 22 of palladium are formed, preferably sputtered, over the upper surface of the $ZrO_2$. The films 21 and 22 are spaced apart one from the other, the space defining a gap located over the depression. The films 21 and 22 are connected at terminals 23 and 24 to an external energizing and current measuring circuit. At the interface between the palladium films 21 and 22 and the $ZrO_2$, a film or layer of palladium oxide 25 and 26 forms.

In operating a $ZrO_2$ oxygen sensor, it is well known that the sensor, that is, the $ZrO_2$ must be raised to an elevated temperature in order to function properly. In the present microsensor structure, the heater member 14 which is within the bridge area 18 of the dielectric layer 13, conducts heat in the upward direction to heat the $ZrO_2$ layer 20. Since the depression or void 17 is directly beneath the heater member 14, the rate of heat energy transmitted downward towards substrate 11 is very small and thus provides a design that minimizes the heater power required to heat the $ZrO_2$ to operating temperature.

Figure 2:
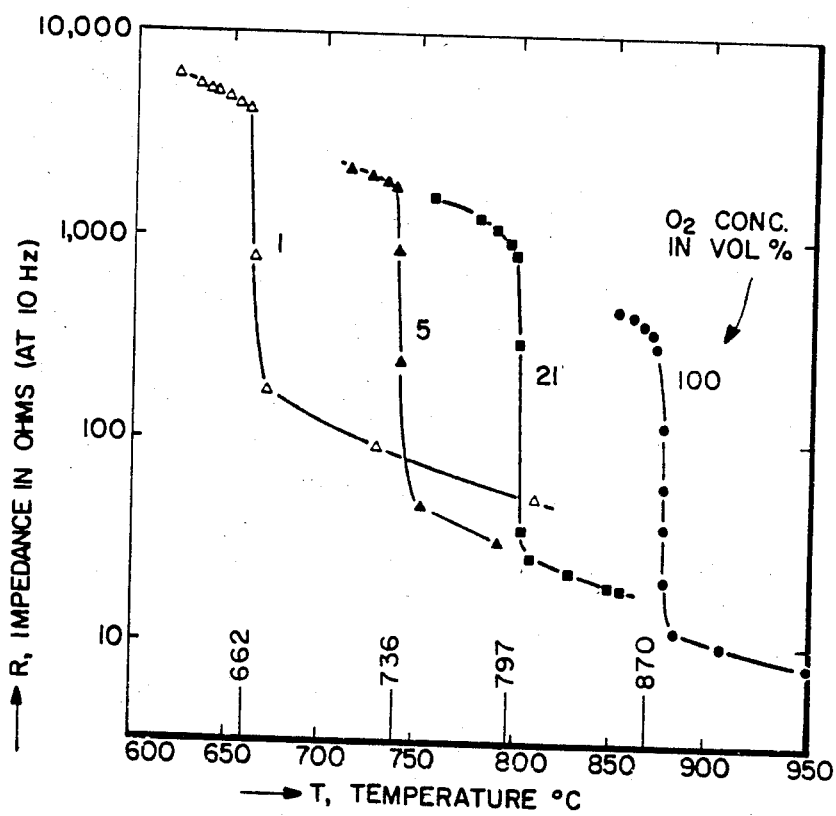
FIG. 2 is a graphical representation of the impedance vs. sensor temperature for various oxygen concentrations, obtained with a conventional, large $ZrO_2$ sensor.[1]

The operation of this $O_2$ sensor is based on the redox (reduction oxidation) reaction of the electrode metal in the presence of $O_2$, at a given temperature, for example 690° C., and influenced by the applied voltage. FIG. 2 is a graphical representation of the impedance vs. sensor temperature at various oxygen concentrations.[1]

(1) H. J. de Bruin and S. P. S. Badwal, "Face Energy of Formation of PdO by Impedance Dispersion Analysis", J. Solid State Chem. 34, 133 (1980)

Examples of the microbridge fabrication, per se, is described in detail in copending application Ser. No. 431,537, filed Sept. 30, 1982, and assigned to the same assignee as the present invention, and details of the microbridge and the formation of the depression by anisotropic etching as taught therein are incorporated herein by reference, as necessary.

The embodiments of the invention in which an exclusive property or right is claimed are defined as follows:

1. An oxygen sensor comprising:
   a semiconductor substrate body with a depression therein;
   a dielectric thin film on said body and bridging said depression;
   a thin film heater embedded within the dielectric film bridge;
   a $ZrO_2$ film over said dielectric film bridge; and,
   first and second conductive films spaced apart one from the other on the surface of said $ZrO_2$ film which is away from the dielectric film.

2. The sensor according to claim 1 in which the space between the first and second conductive films defines a gap located over the depression.

3. The sensor according to claim 1 in which the semiconductor substrate is of silicon.

4. The sensor according to claim 3 in which the dielectric thin film is of silicon dioxide.

5. The sensor according to claim 3 in which the dielectric thin film is of silicon nitride.

6. The sensor according to claim 1 in which the first and second conductive films are palladium films.

7. The sensor according to claim 1 in which at least the first conductive film is a palladium film.

8. An oxygen-sensor comprising:
a silicon substrate body with a depression therein;
a silicon dioxide thin film on said body and bridging said depression;
a thin film heater embedded in the SiO$_2$ film bridge;
a ZrO$_2$ film on said SiO$_2$ film bridge; and,
first and second conductive films spaced apart one from the other on the surface of said ZrO$_2$ film which is away from the SiO$_2$ film, said conductive films selected from the group consisting of palladium, platinum and nickel.

9. An oxygen sensor comprising:
a semiconductor substrate body having a major planar surface with a depression therein;
a dielectric thin film having a heater film embedded therein;
a ZrO$_2$ film, said dielectric film overlaying said substrate major planar surface and bridging said depression so that a hollow exists under said dielectric film at said depression, said ZrO$_2$ film overlaying said dielectric film in the bridging area; and,
a pair of conductive films spaced apart one from the other on the surface of said ZrO$_2$ film which is away from said dielectric film.

10. The sensor according to claim 9 in which the space between said pair of conductive films defines a gap located over the depression.

11. The sensor according to claim 9 in which the semiconductor substrate is of silicon.

12. The sensor according to claim 9 in which the dielectric thin film is of silicon dioxide.

13. The sensor according to claim 9 in which the dielectric thin film is of silicon nitride.

14. The sensor according to claim 9 in which at least one of the pair of conductive films is a palladium film.

15. An oxygen sensor comprising:
a silicon substrate body having a major planar surface with a depression therein;
a thin film of silicon dioxide having a heater film embedded therein;
a ZrO$_2$ film, said silicon dioxide film overlaying said substrate surface and bridging said depression so that a hollow exists under said silicon dioxide film at said depression, said ZrO$_2$ film overlaying said silicon dioxide film in the bridging area; and,
a pair of conductive films spaced apart one from the other on the surface of said ZrO$_2$ film which is away from the SiO$_2$ film.

16. The sensor according to claim 15 in which at least one of the pair of conductive films is a palladium film.

* * * * *